US00PP16536P3

(12) United States Plant Patent
Sumser

(10) Patent No.: US PP16,536 P3
(45) Date of Patent: May 16, 2006

(54) POINSETTIA PLANT NAMED 'FISMILLERL'

(50) Latin Name: *Euphorbia pulcherrima Willd. ex Klotzsch*
Varietal Denomination: Fismillerl

(75) Inventor: Hubert Sumser, Werberstr. 1, 79249 Merzhausen (DE)

(73) Assignee: Hubert Sumser, Merzhausen (DE)

( * ) Notice: Subject to any disclaimer, the term of this patent is extended or adjusted under 35 U.S.C. 154(b) by 0 days.

(21) Appl. No.: 10/932,072

(22) Filed: Sep. 2, 2004

(65) Prior Publication Data

US 2006/0048254 P1 Mar. 2, 2006

(51) Int. Cl.
*A01H 5/00* (2006.01)

(52) U.S. Cl. ..... Plt./307
(58) Field of Classification Search ..... Plt./307
See application file for complete search history.

(56) References Cited

PUBLICATIONS

Community Plant Variety Office—Application No. 2004/0245, filed Feb. 16, 2004, and Denomination Form dated Jun. 15, 2004.
Switzerland—Application No. 03–2071 filed Dec. 12, 2003.
Germany—Application No. EUP 234, filed May 2, 2003, and Denomination Form dated Jan. 15, 2004.
Canada—Application No. 03–3838, filed Sep. 24, 2003, and Canadian Examination dated Apr., 2004; application still pending.
Fisher 2004 and Fisher USA 2004 catalogues offering 'Fiscor Electric' as novelty item (with shipment of plant material beginning in or after May 1, 2004).

*Primary Examiner*—Anne Marie Grunberg
*Assistant Examiner*—June Hwu
(74) *Attorney, Agent, or Firm*—Foley & Lardner, LLP

(57) ABSTRACT

A new and distinct Poinsettia 'Fismillerl' particularly described by the combined features of uniform, red bract color; medium to large sized inflorescence, ovate bracts, uniform, dark-green foliage, ovate leaves almost without lobes; relatively vigorous growth, medium to tall, upright plant habit; and very early flowering response.

1 Drawing Sheet

Latin name of the genus and species of the plant claimed: *Euphorbia pulcherrima Willd. ex Klotzsch.*
Variety denomination: Fismillerl.

BACKGROUND OF THE INVENTION

The present invention relates to a new and distinct cultivar of Poinsettia plant botanically known as *Euphorbia pulcherrima Willd. ex Klotzsch,* and hereinafter referred to by the variety denomination 'Fismillerl'.

'Fismillerl' was discovered by the inventor, Hubert Sumser, from a naturally occurring whole plant mutation in the variety 'Fismille' (patented, U.S. Plant Pat. No. 13,660). 'Fismille' is characterized by large, bright red colored bracts, dark-green foliage almost without lobes, upright and moderately tall plant habit, and early flowering time.

'Fismillerl' was discovered among a group of potted plants of 'Fismille' growing in a greenhouse in Merzhausen, Germany, in 1999. Shading, black-out, by black cloth was applied from Sep. 1, 1999, on, and by mid September one plant began to develop colored bracts while the rest of plants were still green. This plant was observed and after a few weeks taken to Hillscheid for further observation and cultivation. In the summer of 2000, cuttings were taken, rooted and grown out for the trial cultivation in the fall. After discarding 20% of the plants during this first examination, the test was repeated in 2001 and 2002, and thereafter, the new characteristic proved to be uniform and stable.

Asexual reproduction of 'Fismillerl' was performed by vegetative terminal cuttings. Asexual reproduction of 'Fismillerl' was first performed in a greenhouse in July of 2000 in Hillscheid, Germany. Horticultural examination of the plants starting in 2001 and continuing thereafter has demonstrated that the combination of characteristics as herein disclosed for 'Fismillerl' are firmly fixed and retained through successive generations of asexual reproduction. The new cultivar reproduces true to type.

BRIEF SUMMARY OF THE INVENTION

The following traits have been repeatedly observed and are determined to be basic characteristics of 'Fismillerl', which in combination distinguish this Poinsettia as a new and distinct cultivar:

1. uniform, red bract color;
2. medium to large sized inflorescence, ovate bracts;
3. uniform dark-green foliage, ovate leaves almost without lobes;
4. medium sized, rounded plant habit; and
5. very early flowering response.

Plants of the new Poinsettia cultivar 'Fismillerl' differ from plants of the parental cultivar, 'Fismille' in the following characteristics:

1. 'Fismillerl' has a shorter flowering response time and can be marketed 7–10 days earlier than 'Fismille' due to earlier coloring of the bracts.
2. Colored bracts of 'Fismillerl' begin developing along the upper part of the branch, whereas color brachts of 'Fismille' only begin developing along the end of the branch.
3. Young bracts of 'Fismillerl' are medium red in color, RHS 46B, whereas young brachts of 'Fismille' are dark red in color, RHS 46A.
4. There is practically no difference with respect to maturing of the cyathia. However, as a consequence of earlier flowering, plants of 'Fismillerl' may remain somewhat smaller in size than plants of 'Fismille' grown under the same cultivation regime.

5. 'Fismillerl' develops stronger branches than 'Fismille'.

Of the many commercial cultivars known to the inventor, the most similar in comparison to 'Fismillerl' is the parental cultivar 'Fismille'.

'Fismillerl' has not been observed under all possible environmental conditions. The phenotype may vary significantly with variations in environment such as temperature, light intensity, and day-length.

BRIEF DESCRIPTION OF THE DRAWINGS

The accompanying color photographic drawing shows typical inflorescence and foliage of 'Fismillerl', with colors being as true as possible with illustrations of this type. The photograph shows a mature potted plant of 'Fismillerl' in its entirety featuring the uniform red bract color and dark-green foliage.

DETAILED BOTANICAL DESCRIPTION

The following observations, measurements and comparisons describe plants grown in a greenhouse in Langley, British Columbia, Canada, in the fall of 2003. Rooted cuttings were planted into 6 inch (15 cm) pots on July 14, and were pinched on August 5, leaving 7–8 leaves. Short-day conditions were created by applying black cloth beginning September 19. The minimum temperature was initially about 20° C., from October through November only 18–19° C.

Observations and measurements were mainly taken on November 17, when the plants were in full flower and about 18 weeks old. In the following description color references are made to The Royal Horticultural Society Colour Chart (R.H.S.). The color values were determined indoors in a North light.

Plant:
Form: Shrub, self-branching.
Growth habit: About medium to tall sized, upright, not very wide plant habit.
Height (above soil line): 32.6 cm.
Width: 47.2 cm.
Average number of branches: 7.6.
Internode length: 20–25 mm.
Length of branches: 25–27 cm.
Diameter of branches: 7 mm.
Stem color: Lower part light green, RHS 141 C, upper parts of stems are partly reddish infused, the resulting color is approximately RHS 176 C.
Rooting: Medium, sufficiently rooted for transplanting after about 20–24 days in a greenhouse at a temperature of 22–24° C.
Blooming habit: Begin under natural short day conditions in fall: botanically (cyathia open): around November 20, commercially (bracts colored, marketable): about November 10–15.
Flowering response time: About 7 weeks.
Foliage:
Shape: Ovate, most often with truncate base, with very weak lobes and acuminate tip, entire margin.
*Texture.*—Upper surface: smooth and flat, only weakly veined, color of veins: mainly light green, RHS 139 D, at the base red, RHS 45 A.
Lower surface: Flat and smooth, except for the slightly protruding midrib and finer side veins in a pinnate pattern, the vein color is brownish-pink near the base, approximately RHS 179 C, the finer side veins are practically colorless.
Leaf blade size: Length: 13.8 cm; width 9.4 cm.
Petiole: Length: 6.5 cm on average, diameter 0.3 cm.
Quantity: About 35 leaves per plant.
Color: Generally dark green, uniform.
Mature foliage: Upper surface, RHS 139 A; under surface, RHS 139 B.
New foliage: Upper side: RHS 143 A; under side RHS 137 D.
Leaf petiole: Upper side: red-purple, RHS 53 A to 53 B; lower side: RHS 182 B.
Aspect: Petioles are horizontally directed, while the leaf blades slant downwards.
Flowering description: Whole inflorescence with surrounding bracts: medium to large in size, with the bracts mostly horizontally directed or reflexed and slanting downwards; small center with relatively few cyathia.
Average number of inflorescence per plant: 6.9.
Diameter: About 25 cm.
Height of inflorescence: About 3–4 cm.
*Number of bracts per inflorescence.*—9–11 (with a size over 2 cm).
Keeping quality: Good lasting quality will be maintained for about 4 weeks, no dropping of bracts.
Bracts:
Shape: Ovate, with truncate to weakly rounded bases, without or only very weak lobes, and acute to acuminate tips; the bract blade is not flat, but folded along the midrib.
Size of the largest fully colored bract: 13.8 cm long, 8.4 cm wide.
Texture: Moderately rugose or rippled.
Vein color: Upper side corresponds closely to bract color; lower side dull pink, near RHS 51 A.
Color: Generally deep red, uniform; upper surface RHS 46 B; lower surface RHS 46 B to 46 C.
Petiole: 12–16 mm long, color: upper side near RHS 145 A, lower side 147 C.
Cyme: 15–20 mm in diameter, about 10 cyathia borne in a tight cluster.
Cyathium: Ovate, about 6 mm in diameter, medium to light green colored, RHS 143 B, top red, RHS 46 B; total length (with peduncle and female flower): 25 mm.
Peduncle: Light green, RHS 143 C; about 4–5 mm long; 2–3 mm in diameter smooth, glabrous texture; average strength.
Nectar cups: Usually one per cyathium, about 5–6 mm wide, golden yellow to orange colored, RHS 23 A to 25 A, near margin reddish infused: RHS 40 A.
Reproductive organs:
*Stamens.*—About 20 in a cluster, filaments 4 mm, red RHS 46 B; moderate pollen, yellow, RHS 12 A.
*Anthers.*—Shape: capitate at the upper end of the filament; Width: 1.5 mm; Color (before dehiscence): light yellow, RHS 12C.
*Pistil.*—One per cyathium, pistil length: 11 to 12 mm; style length: about 5 mm; color of style and stigma: dark red, RHS 46 A, stigma trifurcate, 6-lobed.
*Ovaries.*—Light to medium green, RHS 143 C, initially obovate, later triangular, diameter3–4 mm, 5–6 mm long, 3 ovules.
*Fruit/seed set.*—No seed set observed.
Disease/pest resistance/susceptibility: No observations made.

I claim:

1. A new and distinct Poinsettia plant named 'Fismillerl' as described and illustrated herein.

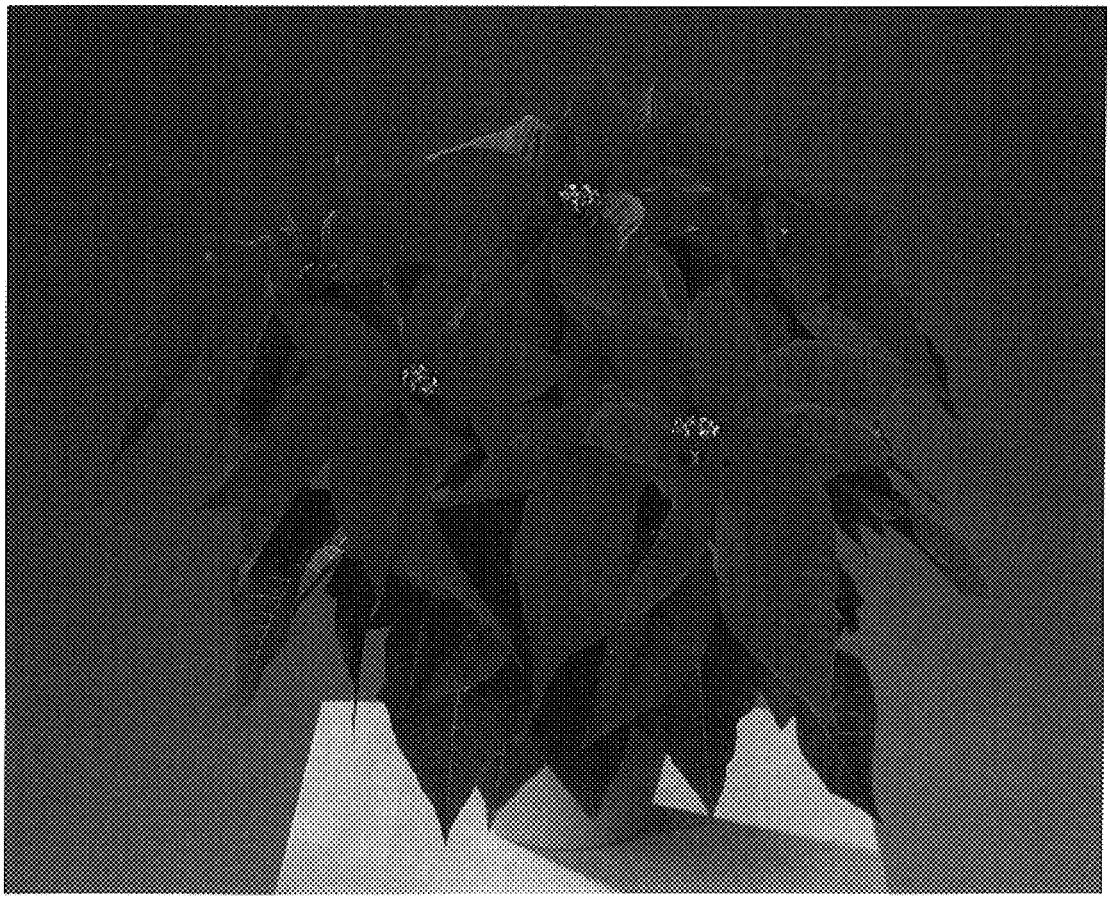

* * * * *